United States Patent [19]

Savins et al.

[11] 4,078,331
[45] Mar. 14, 1978

[54] PROCESS AND CULTURE COMPOSITION FOR GROWTH OF ALGA AND SYNTHESIS OF BIOPOLYMER

[75] Inventors: Joseph George Savins, Dallas; James M. Paul, DeSoto, both of Tex.

[73] Assignee: Mobil Oil Corporation, New York, N.Y.

[21] Appl. No.: 680,820

[22] Filed: Apr. 28, 1976

[51] Int. Cl.² ............................................. A01G 7/00
[52] U.S. Cl. ..................................................... 47/1.4
[58] Field of Search ............................ 47/1.4, 1.2, 58

[56] References Cited

U.S. PATENT DOCUMENTS

| 2,725,677 | 12/1955 | Myers | 47/1.4 |
|---|---|---|---|
| 2,732,661 | 1/1956 | Spoehr et al. | 47/58 |
| 2,732,662 | 1/1956 | Myers et al. | 47/1.4 |
| 2,815,607 | 12/1957 | Schroeder | 47/1.4 |
| 2,949,700 | 8/1960 | Kathrein | 47/1.4 |
| 3,280,502 | 10/1966 | Farrow et al. | 47/1.4 |
| 3,316,674 | 5/1967 | Shirota et al. | 47/1.4 |
| 3,879,890 | 4/1975 | Chen et al. | 47/1.4 |
| 3,889,418 | 6/1975 | Porter et al. | 47/58 |
| 3,958,364 | 5/1976 | Schenck et al. | 47/1.4 |
| 3,958,364 | 5/1976 | Schenck et al. | 47/1.4 |

FOREIGN PATENT DOCUMENTS

| 2,103,462 | 4/1972 | France | 47/1.4 |
|---|---|---|---|

OTHER PUBLICATIONS

The Algae: Arenew, Prescott, 1968, Houghton-Mifflin, pp. 333-335.
Algal Culture . . . , Burlew, 1953, Carnegie Inst. Publ. 600, pp. 98, 108-109.
Ultrastructure of . . . , Gantt et al., 1968, J. Phycol, 4, pp. 65-71.
The Production of . . . , Ramus, 1972, J. Phycol., 8, pp. 97-111.

Primary Examiner—Robert E. Bagwill
Attorney, Agent, or Firm—C. A. Huggett; William D. Jackson

[57] ABSTRACT

This specification discloses a process and a culture composition for growth of an alga and synthesis of biopolymer by the alga. The process involves growth of the alga and concomitant synthesis of the biopolymer in an aqueous culture containing as a source of phosphate for said alga dibasic sodium or dibasic potassium phosphate. The nitrogen source can be sodium nitrate or urea. Control of the pH of the culture is effected by injecting a mixture of carbon dioxide and air into the culture during growth of the alga and synthesis of the biopolymer. The carbon dioxide also serves as a source of carbon for growth of the alga and synthesis of the biopolymer and provides agitation/mixing within the culture chamber. Preferably, the mixture of carbon dioxide and air is injected continuously into the culture during the entire growth period of the alga.

10 Claims, 4 Drawing Figures

PROCESS AND CULTURE COMPOSITION FOR GROWTH OF ALGA AND SYNTHESIS OF BIOPOLYMER

BACKGROUND OF THE INVENTION

1. Field of the Invention

The invention relates to the growth of an alga and synthesis thereby of biopolymer.

2. Description of the Prior Art

Processes for the growth of alga are well known. For example, U.S. Pat. No. 3,195,271 discloses a process for the growth of the alga *Porphyridium cruentum* and synthesis of the alga constituent carrageenin. Other processes for the growth of alga are disclosed in "Algal Culture: From Laboratory to Pilot Plant", J. S. Burlew, Ed., Carnegie Inst. of Washington, Publication No. 600, Washington, D.C. (1964), and "Properties and Products of Algae", J. E. Zajic, Ed., Plenum Press, N.Y. (1970). A culture for the growth of the alga *Porphyridium aerugineum*, known as the MCYII medium, is disclosed by Ramus, J., in the *Jnl. Phycol.*, 8 [1], 97 (1972) and by Gantt, E. et al., in the *Jnl. Phycol.*, 4, 65 (1968).

SUMMARY OF THE INVENTION

The invention comprises a process and culture composition for growth of an alga and concomitantly therewith the synthesis of biopolymer. The alga is grown and the biopolymer synthesized in a culture containing, as a source of phosphate for the alga, dibasic sodium or dibasic potassium phosphate. The nitrogen source can be sodium nitrate or urea. Control of the pH of the culture is effected by injecting into the culture a mixture of carbon dioxide and air during growth of the alga and synthesis of the biopolymer. The carbon dioxide also serves as a source of carbon for growth of the alga and synthesis of the biopolymer. The injected gas also provides a mechanism for culture agitation and cell turnover required to insure exposure of the alga cells to the illumination source. Preferably, injection of the mixture of carbon dioxide and air is continued throughout the entire growth period of the alga.

DESCRIPTION OF THE PREFERRED EMBODIMENTS

Figure 1:
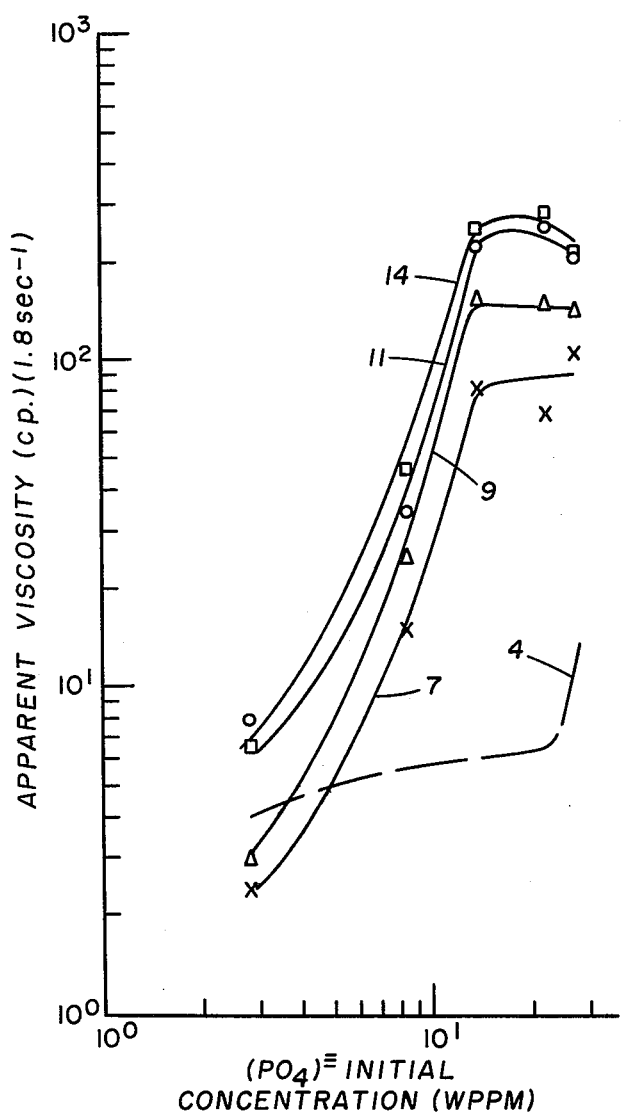
FIG. 1 is a plot of the apparent viscosities attained by cultures of the alga *Porphyridium aerugineum* at various ages of the cultures versus the initial dibasic potassium phosphate concentration of the cultures.

There is disclosed in the copending application of one of us, Joseph George Savins, Ser. No. 680,819, filed concurrently with this application, a process for the production of petroleum from a subterranean formation. In this process, an aqueous driving fluid is injected into the subterranean formation through an input well and passed through the formation in the direction of an output well to drive the petroleum in the formation to the output well. The aqueous driving fluid contains a thickening agent and the thickening agent is a biopolymer, a heteropolysaccharide, synthesized by an alga. The alga, in its growth cycle, in a culture thereof, concomitantly synthesizes the biopolymer as an extracellular product and the biopolymer enters into solution in the culture. The aqueous driving fluid may contain the biopolymer as an in-vivo solution or in a reconstituted form. The disclosure of the mentioned copending application is included by reference thereto in the present application.

The present invention is directed to a process and culture composition for the growth of alga and synthesis of biopolymer. The biopolymer may be employed as a thickening agent in aqueous driving fluids for the recovery of petroleum from a subterranean formation. However, it is to be understood that the biopolymer has other uses than as a thickening agent in the recovery of petroleum, such other uses for alga biopolymer being known to the art.

Whereas the process of the invention may be employed for the growth of, and synthesis of biopolymer by, any alga, it is particularly applicable to the growth of, and synthesis of biopolymer by, the alga *Porphyridium aerugineum*. The alga *Porphyridium aerugineum*, in common with other algae, requires for its growth illumination, an inorganic carbon source and certain other nutrients and nutrient-related materials. Since *Porphyridium aerugineum* is an obligate photoautotroph, it is customary to provide the source of inorganic carbon in the form of gaseous carbon dioxide. A standard culture for the growth of *Porphyridium aerugineum* is the MCYII medium previously mentioned. This culture contains the following distribution of macro and micro levels of inorganic ions, chelating agents, buffering agent, vitamins, etc.

TABLE I

| MCYII MEDIUM | | |
| --- | --- | --- |
| $NaNO_3$ | 442 | mg |
| KCl | 30 | mg |
| $CaCl_2 . 2H_2O$ | 36.6 | mg |
| $FeCl_3 . 6H_2O$ | 1.9 | mg |
| $MgSO_4 . 7H_2O$ | 100 | mg |
| $Na_2$ . glycerophosphate . $5H_2O$ | 90 | mg |
| Tricine buffer | 986 | mg |
| PII trace metal mix | 10 | ml |
| Vitamin $B_{12}$ | 3.5 | μg |
| Distilled water to | 1000 | ml |
| Adjust pH to 7.6 with NaOH | | |
| PII Metal Mix: | | |
| $H_3BO_3$ | 114.0 | mg |
| $MnCl_2 . 4H_2O$ | 14.4 | mg |
| $ZnSO_4$ | 2.2 | mg |
| $CoCl_2 . 6H_2O$ | 0.4 | mg |
| $FeCl_3 . 6H_2O$ | 4.8 | mg |
| $Na_2EDTA$ | 100 | mg |
| Distilled water to | 100 | ml |

In accordance with one aspect of the present invention, an alga, such as *Porphyridium aerugineum*, is grown and biopolymer synthesized in an aqueous culture containing dissolved therein dibasic sodium or dibasic potassium phosphate as a source of phosphate for the alga. The culture also contains dissolved therein hydrated magnesium sulfate, sodium nitrate or urea, calcium chloride, ferric chloride or ethylene dinitrilo tetraacetic acid Ferric-Sodium salt ($C_{10}H_{12}FeN_2NaO_8$), boric acid, hydrated ferrous sulfate, hydrated zinc sulfate, potassium chloride, manganous chloride, vitamin $B_{12}$, hydrated cobaltous chloride, and disodium salt of ethylene diamine tetraacetic acid. The amount of dibasic potassium or dibasic sodium phosphate employed is such that the initial phosphate ion concentration in the aqueous culture is at least 14 weight parts per million.

In this culture, the phosphate requirements of the alga, as indicated, are provided by the dibasic sodium or dibasic potassium phosphate. The latter two compounds are relatively inexpensive as compared to sodium glycerophosphate, the phosphate source employed in the prior art culture set forth in Table I. Further, in this aspect of the present invention, pH control, or buffering, is effected by injection of a mixture of carbon dioxide and air into the culture during growth of the alga. Control of the pH of the culture by injection of a mixture of carbon dioxide and air is relatively inexpensive as compared to the tricine buffer employed in the prior art culture set forth in Table I. Accordingly, growth of the alga and synthesis of the biopolymer by the process of the invention is effected employing low cost components in the culture, thereby enabling the synthesis of biopolymer at low cost. Thus, the process of the invention is particularly applicable to the synthesis of biopolymer for such uses as a thickening agent in an aqueous driving fluid for the recovery of petroleum from a subterranean process where economics prohibits high cost materials and methods.

In a specific embodiment, the culture contains the components, and in the concentrations indicated, set forth in Table II following.

TABLE II

| Component | Concentration - WPPM |
|---|---|
| $MgSO_4 . 7H_2O$ | 100 |
| $NaNO_3$ or | 442 |
| Urea | 155 |
| $CaCl_2$ | 28 |
| $FeCl_3$ or | 1.43 |
| $C_{10}H_{12}FeN_2NaO_8$ | 5.36 |
| $K_2HPO_4$ or | At least 26 |
| $Na_2HPO_4$ | At least 21 |
| $H_3BO_3$ | 11.4 |
| $FeSO_4 . 7H_2O$ | 2.2 |
| $ZnSO_4 . 7H_2O$ | 1.44 |
| KCl | 30 |
| $B_{12}$ | $3.5 \times 10^{-6}$ |
| $CoCl_2 . 6H_2O$ | 0.044 |
| $(Na)_2EDTA$ (disodium salt of ethylene diamine tetraacetic acid) | 10 |

Injection of the mixture of carbon dioxide and air into the aqueous culture during growth of the alga and synthesis of the biopolymer is preferably carried out continuously during the entire growth period of the alga. Growth of the alga and synthesis of the biopolymer can be carried out under artificial illumination in which case the illumination and the injection of the mixture of carbon dioxide and air can be provided during the entire growth period of the alga. On the other hand, growth of the alga and synthesis of the biopolymer can be carried out with natural illumination in which case the growth and synthesis occur in a diurnal cycle. $CO_2$/air is always continuously injected, with or without tricine buffer, diurnal or continuous illumination, as the carbon is required for nutrition. We have ascertained that by continuous injection of the mixture of carbon dioxide and air during both the daylight and dark portions of the diurnal cycle, fluctuations in pH of the culture are eliminated and both the production of alga and kinetics and levels of biopolymer synthesis are improved.

The relative proportions of the carbon dioxide and air in the mixture thereof injected into the aqueous culture may be as desired. However, it is preferred that the mixture contain 5% of carbon dioxide and 95% of air.

The following examples will be illustrative of the invention.

EXAMPLE 1

This example will illustrate the effect of the concentration of dibasic potassium phosphate in the aqueous culture on the extent of synthesis of biopolymer with time.

*Porphyridium aerugineum* was grown and biopolymer synthesized in a series of cultures containing different initial concentrations of dibasic potassium phosphate. These concentrations of dibasic potassium phosphate, in terms of phosphate ion $(PO_4)^=$ in weight parts per million, were 28, 22.5, 14.0, 8.4, and 2.8. The cultures contained 442 weight parts per million of sodium nitrate and also contained the remaining components, and in the concentrations, set forth in Table II above. The particular *Porphyridium aerugineum* that was employed is cataloged as isolate No. 755 in the alga culture collection maintained at Indiana State University, Bloomington, Indiana, e.g. see Starr, R. C., *Amer. Jnl. Bot.*, 51 [9], 1013 (1964). The alga was grown and the biopolymer synthesized at an average temperature of 77° F. (25° C.). Agitation was provided by the standard shake flask culture method. The carbon source was 5% carbon dioxide entrained with 95% air and was injected continuously into the cultures. This also provided a measure of agitation. Undefined but continuous (24-hour) illumination was provided via ceiling mounted and auxiliary fluorescent lights. Levels of illumination and radiant energy incident to the culture flasks were on the order of 800-foot candles (8061.12 lux) and $10^4$ ergs/cm$^2$ sec. ($10^3$ microjoules/cm$^2$ sec.). Samples of the cultures were removed at 4, 7, 9, 11, and 14-day intervals and the apparent viscosity at a shear rate of 1.8 sec$^{-1}$ measured employing a Brookfield viscometer fitted with a U.L. adapter. The apparent viscosity of the culture is a measure of the amount of biopolymer in the culture.

Figure 2:
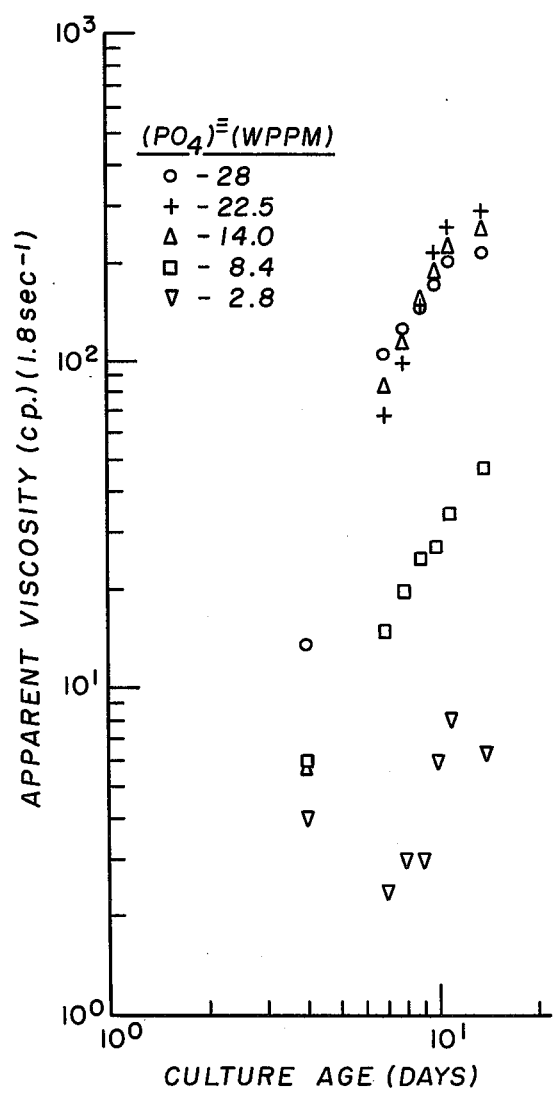
FIG. 2 is a plot of the apparent viscosities attained by cultures of the alga *Porphyridium aerugineum* at various initial concentrations of dibasic potassium phosphate in the cultures versus age of the cultures.

The results are given in FIGS. 1 and 2. In FIG. 1, the concentration of the dibasic potassium phosphate is expressed as concentration of $PO_4^{57}$ ion. It will be observed from FIGS. 1 and 2 that an initial $PO_4^{57}$ level on the order of 14 weight parts per million, i.e., 26 weight parts per million of dibasic potassium phosphate leads to an acceptable level of viscosity production, i.e., concentration of biopolymer in the culture.

EXAMPLE 2

In this example, *Porphyridium aerugineum* was grown in a series of three cultures. One of the cultures contained 41 weight parts per million of dibasic potassium phosphate (22.5 weight parts per million of $PO_4^{57}$). Another culture contained 51 weight parts per million of dibasic potassium phosphate (28.0 weight parts per million of $PO_4^{57}$). The third culture contained 42 weight parts per million of dibasic sodium phosphate (28.0 weight parts per million of $PO_4^{57}$). Each of the cultures contained 442 weight parts per million of sodium nitrate and the remaining components set forth in Table II and in the concentrations given. The particular *Porphyridium aerugineum* that was employed was the same isolate that was employed in Example 1. Conditions of temperature, illumination, agitation and injection of a mixture of carbon dioxide and air were the same as in Example 1. Samples of the cultures were removed at various intervals and the apparent viscosities measured as in Example 1.

Figure 3:
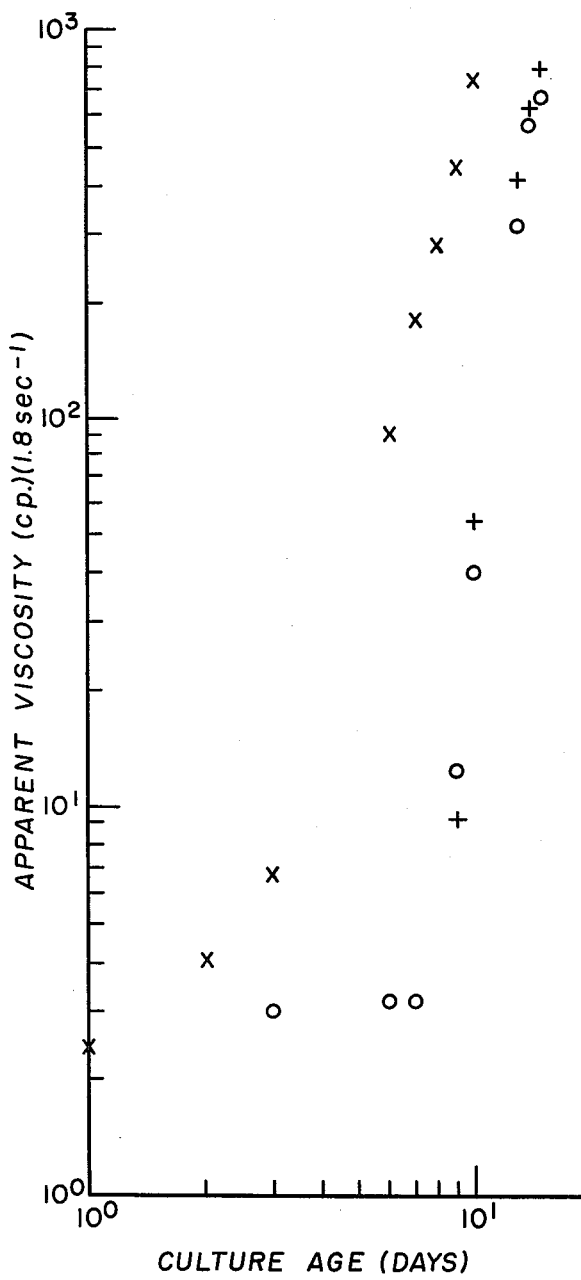
FIG. 3 is a plot of the apparent viscosities attained by cultures of the alga *Porphyridium aerugineum* containing dibasic sodium and dibasic potassium phosphate.

The results are given in FIG. 3. In FIG. 3, the data points for the 41 weight parts per million of dibasic potassium phosphate are signified by o, for the 51 weight parts per million of dibasic potassium phosphate by +, and for the dibasic sodium phosphate by X. It will be observed from the Figure that the viscosity kinetics and production levels are practically the same for the three sources of the $PO_4^{57}$ ion.

EXAMPLE 3

This example will illustrate the effect of employing urea as the source of nitrogen in the aqueous culture on the extent of synthesis of biopolymer with time.

*Porphyridium aerugineum* was grown and biopolymer synthesized in two aqueous cultures. Each of the cultures contained 155 weight parts per million of urea. One of the cultures contained 51 weight parts per million of dibasic potassium phosphate and the other contained 42 weight parts per million of dibasic sodium phosphate. Each also contained the remaining components set forth in Table II and in the concentrations given. The particular *Porphyridium aerugineum* and the reaction conditions and procedures employed were the same as in the previous examples.

Figure 4:
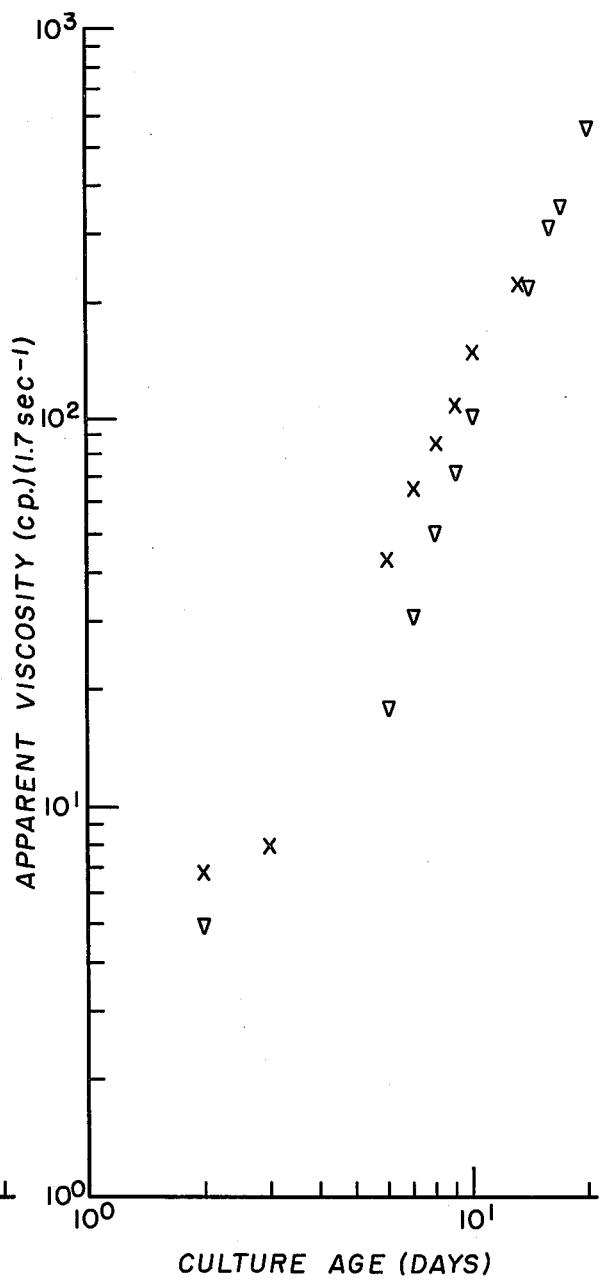
FIG. 4 is a plot of the apparent viscosities attained by cultures of the alga *Porphyridium aerugineum* containing urea as a nitrogen source.

The results are given in FIG. 4. In this Figure, the data points for the culture containing the dibasic potassium phosphate are signified by X and for the dibasic sodium phosphate by ▽. It will be observed from the Figure that the viscosity kinetics and production levels are practically the same when urea is used as the nitrogen source.

We claim:

1. The process comprising growing the alga *Porphyridium aerugineum* and synthesizing biopolymer in an aqueous culture containing dissolved therein as a phosphate source for said alga dibasic potassium or dibasic sodium phosphate and injecting a mixture of carbon dioxide and air into said aqueous culture continuously during the entire growth period of said alga and synthesis of said biopolymer to control the pH of said culture.

2. The process of claim 1 wherein said aqueous culture contains said dibasic potassium phosphate or said dibasic sodium phosphate in an amount such that the initial concentration of phosphate ion in said aqueous culture is at least 14 weight parts per million.

3. The process of claim 1 wherein said aqueous culture also contains hydrated magnesium sulfate, sodium nitrate or urea, calcium chloride, ferric chloride or ethylene dinitrilo tetraacetic acid Ferric-Sodium salt, boric acid, hydrated ferrous sulfate, hydrated zinc sulfate, potassium chloride, manganous chloride, vitamin $B_{12}$, hydrated cobaltous chloride, and disodium salt of ethylene diamine tetraacetic acid.

4. The process of claim 3 wherein said hydrated magnesium sulfate is in the amount of 100 weight parts per million, said sodium nitrate is in the amount of 442 weight parts per million or said urea is in the amount of 155 weight parts per million, said calcium chloride is in the amount of 28 parts per million, said ferric chloride is in the amount of 1.43 weight parts per million or said ethylene dinitrilo tetraacetic acid Ferric-Sodium salt is in the amount of 5.36 weight parts per million, said boric acid is in the amount of 11.4 weight parts per million, said hydrated ferrous sulfate is in the amount of 2.2 weight parts per million, said hydrated zinc sulfate is in the amount of 1.44 weight parts per million, said potassium chloride is in the amount of 30 weight parts per million, said vitamin $B_{12}$ is in the amount of $3.5 \times 10^{-6}$ weight parts per million, said hydrated cobaltous chloride is in the amount of 0.044 weight parts per million, and said disodium salt of ethylene diamine tetraacetic acid is in the amount of 10 weight parts per million.

5. The process of claim 1 wherein said aqueous culture also contains hydrated magnesium sulfate, urea, calcium chloride, ethylene dinitrilo tetraacetic acid Ferric-Sodium salt, boric acid, hydrated ferrous sulfate, hydrated zinc sulfate, potassium chloride, manganous chloride, vitamin $B_{12}$, hydrated cobaltous chloride, and disodium salt of ethylene diamine tetraacetic acid.

6. The process of claim 5 wherein said hydrated magnesium sulfate is in the amount of 100 weight parts per million, said urea is in the amount of 155 weight parts per million, said calcium chloride is in the amount of 28 weight parts per million, said ethylene dinitrilo tetraacetic acid Ferric-Sodium salt is in the amount of 5.36 weight parts per million, said boric acid is in the amount of 11.4 weight parts per million, said hydrated ferrous sulfate is in the amount of 2.2 weight parts per million, said hydrated zinc sulfate is in the amount of 1.44 weight parts per million, said potassium chloride is in the amount of 30 weight parts per million, said vitamin $B_{12}$ is in the amount of $3.5 \times 10^{-6}$ weight parts per million, said hydrated cobaltous chloride is in the amount of 0.044 weight parts per million, and said disodium salt of ethylene diamine tetraacetic acid is in the amount of 10 weight parts per million.

7. A culture for the growth of an alga and synthesis of biopolymer comprising an aqueous solution of hydrated magnesium sulfate, sodium nitrate or urea, calcium chloride, ferric chloride or ethylene dinitrilo tetraacetic acid Ferric-Sodium salt, dibasic potassium or dibasic sodium phosphate, boric acid, hydrated ferrous sulfate, hydrated zinc sulfate, potassium chloride, vitamin $B_{12}$, hydrated cobaltous chloride, and disodium salt of ethylene diamine tetraacetic acid, said culture containing an injected mixture of carbon dioxide and air.

8. A culture for the growth of an alga and synthesis of biopolymer comprising an aqueous solution containing 100 weight parts per million of hydrated magnesium sulfate, 442 weight parts per million of sodium nitrate or 155 weight parts per million of urea, 28 weight parts per million of calcium chloride, 1.43 weight parts per million of ferric chloride or 5.36 weight parts per million of ethylene dinitrilo tetraacetic acid Ferric-Sodium salt, at least 26 weight parts per million of dibasic potassium phosphate or 21 weight parts per million of dibasic sodium phosphate, 11.4 weight parts per million of boric acid, 2.2 weight parts per million of hydrated ferrous sulfate, 1.44 weight parts per million of hydrated zinc sulfate, 30 weight parts per million of potassium chloride, $3.5 \times 10^{-6}$ weight parts per million of vitamin $B_{12}$, 0.044 weight parts per million of hydrated cobaltous chloride, and 10 weight parts per million of disodium salt of ethylene diamine tetraacetic acid, said culture containing an injected mixture of carbon dioxide and air.

9. A culture for the growth of an alga and synthesis of biopolymer comprising an aqueous solution of hydrated magnesium sulfate, urea, calcium chloride, ethylene dinitrilo tetraacetic acid Ferric-Sodium salt, dibasic potassium or dibasic sodium phosphate, boric acid, hydrated ferrous sulfate, hydrated zinc sulfate, potassium chloride, vitamin $B_{12}$, hydrated cobaltous chloride, and disodium salt of ethylene diamine tetraacetic acid, said culture containing an injected mixture of carbon dioxide and air.

10. A culture for the growth of an alga and synthesis of biopolymer comprising an aqueous solution containing 100 weight parts per million of hydrated magnesium sulfate, 155 weight parts per million of urea, 28 weight parts per million of calcium chloride, 5.36 weight parts per million of ethylene dinitrilo tetraacetic acid Ferric-Sodium salt, at least 26 weight parts per million of dibasic potassium phosphate or 21 weight parts per million of dibasic sodium phosphate, 11.4 weight parts per million of boric acid, 2.2 weight parts per million of hydrated ferrous sulfate, 1.44 weight parts per million of hydrated zinc sulfate, 30 weight parts per million of potassium chloride, $3.5 \times 10^{31\ 6}$ weight parts per million of vitamin $B_{12}$, 0.044 weight parts per million of hydrated cobaltous chloride, and 10 weight parts per million of disodium salt of ethylene diamine tetraacetic acid, said culture containing an injected mixture of carbon dioxide and air.

* * * * *

UNITED STATES PATENT AND TRADEMARK OFFICE
CERTIFICATE OF CORRECTION

PATENT NO. : 4,078,331
DATED : March 14, 1978
INVENTOR(S) : Joseph George Savins and James M. Paul It is certified that error appears in the above-identified patent and that said Letters Patent are hereby corrected as shown below:

In the Title Page, column 2, under OTHER PUBLICATIONS, "The Algae: Arenew" should read --The Algae: A Review--.

Column 2, in Table I, second column, "0.4" should be --0.44--.

Column 4, lines 44, 45, 55, 58, 60, and column 5, line 10, "$PO_4^{57}$" should read --$PO_4^{=}$--.

Column 8, line 5, "$3.5 \times 10^{316}$" should be --$3.5 \times 10^{-6}$--.

Signed and Sealed this

Fourth Day of July 1978

[SEAL]

Attest:

RUTH C. MASON
Attesting Officer

DONALD W. BANNER
Commissioner of Patents and Trademarks